US008808195B2

(12) United States Patent
Tseng et al.

(10) Patent No.: US 8,808,195 B2
(45) Date of Patent: Aug. 19, 2014

(54) EYE-TRACKING METHOD AND SYSTEM FOR SCREENING HUMAN DISEASES

(76) Inventors: Po-He Tseng, Los Angeles, CA (US); Ian G. M. Cameron, Kingston (CA); Douglas P. Munoz, Kingston (CA); Laurent Itti, Los Angeles, CA (US)

( * ) Notice: Subject to any disclaimer, the term of this patent is extended or adjusted under 35 U.S.C. 154(b) by 1143 days.

(21) Appl. No.: 12/656,109

(22) Filed: Jan. 15, 2010

(65) Prior Publication Data

US 2010/0208205 A1   Aug. 19, 2010

Related U.S. Application Data

(60) Provisional application No. 61/145,011, filed on Jan. 15, 2009.

(51) Int. Cl.
*A61B 3/113* (2006.01)

(52) U.S. Cl.
CPC ..................... *A61B 3/113* (2013.01)
USPC .......................................................... 600/558

(58) Field of Classification Search
USPC ................................................. 600/558, 595
See application file for complete search history.

(56) References Cited

U.S. PATENT DOCUMENTS

| | | | |
|---|---|---|---|
| 7,319,780 B2 * | 1/2008 | Fedorovskaya et al. | 382/128 |
| 7,549,743 B2 * | 6/2009 | Huxlin et al. | 351/203 |
| 7,922,670 B2 * | 4/2011 | Jones et al. | 600/558 |
| 2005/0047647 A1 * | 3/2005 | Rutishauser et al. | 382/159 |
| 2006/0189886 A1 * | 8/2006 | Jones et al. | 600/558 |
| 2006/0233422 A1 * | 10/2006 | Toyama | 382/103 |
| 2006/0270945 A1 * | 11/2006 | Ghajar | 600/558 |
| 2007/0066916 A1 * | 3/2007 | Lemos | 600/558 |
| 2007/0173699 A1 * | 7/2007 | Mathan et al. | 600/300 |
| 2007/0201731 A1 * | 8/2007 | Fedorovskaya et al. | 382/118 |
| 2008/0278682 A1 * | 11/2008 | Huxlin et al. | 351/203 |
| 2008/0304740 A1 * | 12/2008 | Sun et al. | 382/168 |
| 2009/0132275 A1 * | 5/2009 | Jung et al. | 705/2 |
| 2009/0158179 A1 * | 6/2009 | Brooks | 715/762 |
| 2009/0164403 A1 * | 6/2009 | Jung et al. | 706/46 |
| 2009/0164503 A1 * | 6/2009 | Jung et al. | 707/102 |
| 2009/0169125 A1 * | 7/2009 | Huguenel et al. | 382/251 |

(Continued)

OTHER PUBLICATIONS

Turano et al. "Fixation behavior while walking: persons with central visual field loss" Vision Research 42 (2002) 2635-2644.*

(Continued)

*Primary Examiner* — Sean Dougherty
*Assistant Examiner* — Michael C Stout

(57) ABSTRACT

This invention provides methods, system, and apparatus for assessing and/or diagnosing a neurobehavioural disorder in a subject. The methods, systems, and apparatus include the subject freely observing a visual scene, without having to carry out a task or follow specific instructions. In one embodiment, a computational model is used to select one or more feature in a visual scene and generate a spatial map having first map values that are predictive of eye movement end points of a hypothetical observer relative to the one or more feature. A subject's eye movements are recorded while the subject freely observes the visual scene, and a difference between second map values that correspond to the subject's eye movement endpoints and a set of map values selected randomly from the first map values is quantified, wherein the difference is indicative of a neurobehavioural disorder in the subject. Neurobehavioural disorders such as Parkinson's disease, Alzheimer's disease, Huntington's disease, fetal alcohol spectrum disorder, attention deficit hyperactivity disorder, schizophrenia, autism, Tourette syndrome, and progressive supranuclear palsy may be assessed and/or diagnosed.

25 Claims, 5 Drawing Sheets

(56) References Cited

U.S. PATENT DOCUMENTS

| | | |
|---|---|---|
| 2009/0185748 A1* | 7/2009 | Kortum et al. ............... 382/232 |
| 2009/0318773 A1* | 12/2009 | Jung et al. ................... 600/300 |
| 2010/0056274 A1* | 3/2010 | Uusitalo et al. ............... 463/31 |
| 2010/0086200 A1* | 4/2010 | Stankiewicz et al. ......... 382/154 |
| 2010/0086221 A1* | 4/2010 | Stankiewicz et al. ......... 382/224 |
| 2010/0189354 A1* | 7/2010 | de Campos et al. ........... 382/190 |
| 2011/0172556 A1* | 7/2011 | Jones et al. .................. 600/558 |

OTHER PUBLICATIONS

Carmi et al. "Visual causes versus correlates of attention selection in dynamic scenes" Vision Research 46 (2006) 4333-4345.*

American Psychiatric Association. Diagnostic and Statistical Manual of Mental Disorders. 4th Edition. Washington, DC: American Psychiatric Association; 1994.

Briand, K. A., Strallow, D., Hening, W., Poizner, H., & Sereno, A. B. (1999). Control of voluntary and reflexive saccades in Parkinson's disease. Exp. Brain Res. 129, 38-48.

Brien, D., Glasgow, J., and Munoz, D. P. (2005) The application of a case-based reasoning system to attention deficit hyperactivity disorder. Case-based reasoning research and development: 6th international conference on case-based reasoning, ICCBR 2005, Chicago, Lecture notes in Computer Science, Springer-Verlag,(3620): 122-136.

Chan, F., Armstrong, I. T., Pari, G., Riopelle, R. J., and Munoz, D. P. (2005) Saccadic eye movement tasks reveal deficits in automatic response inhibition in Parkinson's disease. Neuropsychologia 43: 784-796.

Chudley AE, Conry J, Cook JL, Loock C, Rosales T, LeBlanc N (2005) Fetal alcohol spectrum disorder: Canadian guidelines for diagnosis. Can Med Assoc J 172:S1-S21.

Fukushima, J., Fukushima, K., Miyasaka, K., & Yamashita, I. (1994). Voluntary control of saccadic eye movement in patients with frontal cortical lesions and parkinsonian patients in comparison with that in schizophrenics. Biol.Psychiatr. 36, 21-30.

Green, C. R., Munoz, D. P., Nikkei, S.M., and Reynolds, J. N. (2007) Deficits in eye movement control in children with Fetal Alcohol Spectrum Disorders. Alcoholism: Clinical and Exp. Res. 31: 500-511.

Itti, L., & Koch, C. (2001) Computational Modeling of Visual Attention. Nature Reviews Neuroscience, 2(3), 194-203.

LeVasseur, A. L., Flanagan, J. R., Riopelle, R. J., and Munoz, D. P. (2001) Control of volitional and reflexive saccades in Tourette's syndrome. Brain 124: 2045-2058.

Mostofsky, S. H., Lasker, A. G., Singer, H. S., Denckla, M. B. & Zee, D. S. (2001). Oculomotor abnormalities in boys with Tourette syndrome with and without ADHD. J Am Acad Child Adolesc Psychiatry, 40, 1464-1472.

Munoz, D. P., Armstrong, I. T., Hampton, K. A., & Moore, K. D. (2003) Altered control of visual fixation and saccadic eye movements in attention-deficit hyperactivity disorder. J. Neurophysiol. 90: 503-514.

Noton, D., & Stark, L. (1971) Scanpaths in eye movements during pattern perception. Science, 171(968), 308-11.

Peltsch, A., Hoffman, A., Armstrong, I., Pari, G., and Munoz, D. P. (2008) Saccadic impairments in Huntington's disease correlate with disease severity. Exp. Brain Res. (in press).

Peters, R. J., & Itti, L. (2007) Beyond bottom-up: Incorporating task-dependent influences into a computational model of spatial attention. In: Proc. IEEE Conference on Computer Vision and Pattern Recognition (CVPR).

Peters, R. J., Iyer, A., Itti, L., & Koch, C. (2005) Components of bottom-up gaze allocation in natural images. Vision Research, 45(8), 2397-2416.

Privitera, C. M., & Stark, L. W. (2000) Algorithms for defining visual regions-of-interest: comparison with eye fixations. IEEE Trans Patt Anal Mach Intell, 22(9), 970-982.

Munoz, D. P., Armstrong, I., and Coe, B. (2007) Using eye movements to probe development and dysfunction. In: Eye movements: A window on mind and brain. Eds: Van Gompel, R.P.G., Fischer, M.H., Murray, W.S., & Hill, R.L. Oxford: Elsevier pp. 99-124.

* cited by examiner

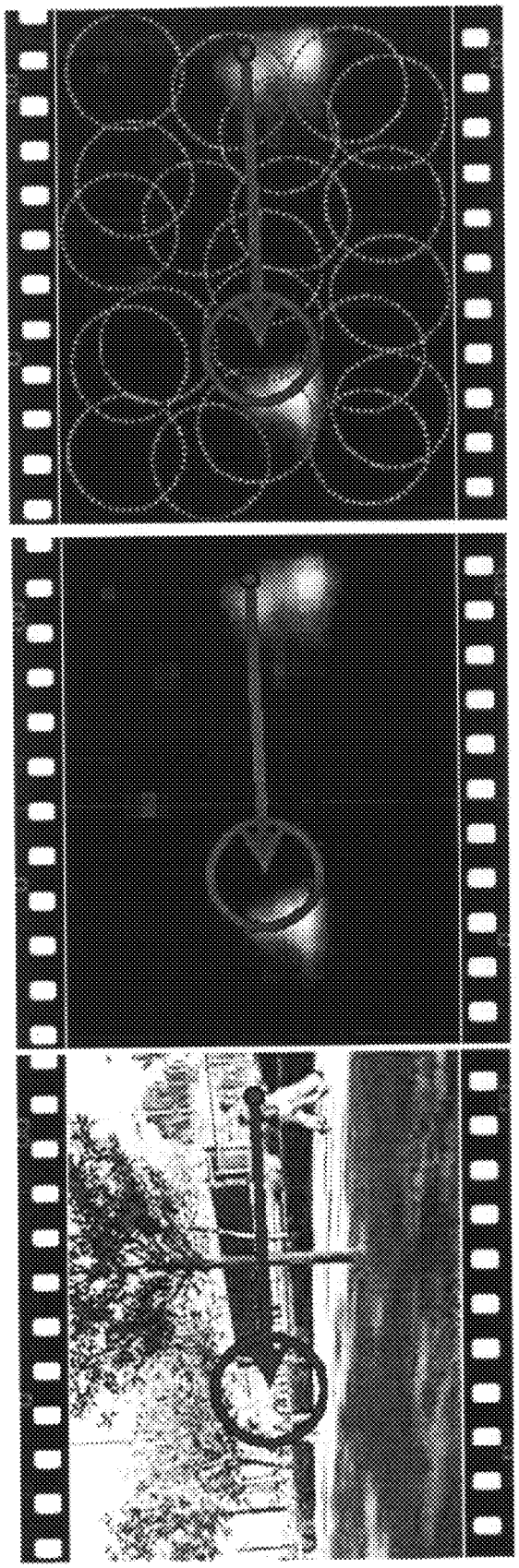

EYE-TRACKING METHOD AND SYSTEM FOR SCREENING HUMAN DISEASES

RELATED APPLICATIONS

This application claims the benefit of the filing date of U.S. Provisional Patent Application No. 61/145,011, filed Jan. 15, 2009, the contents of which are incorporated herein by reference in their entirety.

STATEMENT REGARDING SPONSORED RESEARCH

This invention was made with U.S. government support under Grant No. ILS-0515261 awarded by the National Science Foundation and was also made under Grant No. HFSP 0039/2005 by the Human Frontier Science Program. The U.S. government has certain rights in the invention.

FIELD OF THE INVENTION

This invention provides methods, system, and apparatus for assessing and/or diagnosing a neurobehavioural disorder in a subject. As described herein, the methods, systems, and apparatus include the subject freely observing a visual scene, without having to carry out a task or follow specific instructions.

BACKGROUND

Eye movements and certain complex visual functions are influenced by neurobehavioural disorders such as (but not limited to) Parkinson's disease (PD), Alzheimer's disease (AD), fetal alcohol spectrum disorder (FASD), and attention deficit hyperactivity disorder (ADHD). Symptoms of Parkinson's disease include motor impairments, such as muscle rigidity and slowness of movement, impaired ability to suppress automatic behavioral responses, and difficulty in initiating voluntary actions, such as saccades. Saccades are rapid, ballistic eye-movements that bring the part of the retina with the highest acuity (the fovea) onto a target of interest, and are the most common type of eye-movement in human life with hundreds of thousands of saccades initiated per day. Individuals with FASD present with a wide range of cognitive impairments that include deficits in spatial working memory, planning, response inhibition and the ability to think abstractly and flexibly. ADHD is a highly prevalent neurobehavioural disorder characterized by inattention, hyperactivity, and impulsivity that may have an incidence as high as 5-10% in children and 2-4% in adults worldwide. Previous studies have explored these disorders and their relationship to top-down (goal oriented) and bottom-up (stimulus driven) attention by utilizing different visual and cognitive tasks. The tasks require participants to be restricted to performing specific behaviours that are varied across experiments.

Because of the dysfunction in voluntary control and response inhibition across these disorders, it is assumed that they are more governed by "stimulus-driven", rather than "goal-driven" processes, and as such may be more governed by stimuli that are highly 'salient', i.e., capable of capturing attention. This can occur in a variety of neurobehavioral disorders, including schizophrenia, Alzheimer's disease, Huntington's disease (HD), autism, Tourette syndrome (TS) and progressive supranuclear palsy (PSP). However, the nature of the task can dictate whether these disorders surface or not, and this often leads to contradictory results. Each of these disorders also show that processing time of goal-driven behaviour seems to be slower; however, different conditions across tasks can lead to different measures of attentional deficits. Thus, while previous studies are valuable in dissecting particular impairments in attentional allocation, the often contradictory results show how difficult it is to use one parameter to identify underlying behavioural differences between diseases.

SUMMARY

Described herein is a method of assessing and/or diagnosing a neurobehavioural disorder in a subject, comprising: using a computational model to select one or more feature in a visual scene and generate a spatial map having first map values that are predictive of eye movement end points of a hypothetical observer relative to the one or more feature; recording the subject's eye movements while the subject freely observes the visual scene; and quantifying a difference between second map values that correspond to the subject's eye movement endpoints and a set of map values selected randomly from the first map values; wherein the difference is indicative of a neurobehavioural disorder in the subject. The difference may be indicative of the extent to which the subject was guided towards the selected one or more feature while observing the visual scene.

Also described herein is a system that classifies a subject into a neurobehavioural disorder group. The system includes a video display and eye-tracking hardware to monitor eye-movements of subjects watching visual scenes, and a processor-based computational model of one or more measures of the visual scenes displayed on the video display. In one embodiment, at least one measure is saliency, in the form of a topographic map in correspondence with the visual scene and in which the activity or value at any location is indicative of the computed visual conspicuity, attractiveness, or saliency of that location (Itti and Koch, 2001). The processor compares an output of the computational model to the eye movement patterns of a subject. In one embodiment, the comparison provides an assessment of the extent to which the subject was guided towards particular (e.g., more salient) stimuli while observing the visual scenes. A result of the comparison is indicative of whether or not the subject has a neurobehavioural disorder. A result of the comparison is also indicative of the type of neurobehavioural disorder in the subject.

Also described herein is a system for assessing and/or diagnosing a neurobehavioural disorder in a subject, comprising: a computational model that selects one or more feature in a visual scene and generates a spatial map having first map values that are predictive of eye movement end points of a hypothetical observer relative to the one or more feature; an eye tracker that records the subject's eye movements while the subject freely observes the visual scene; and a processor that quantifies a difference between second map values that correspond to the subject's eye movement endpoints and a subset of map values selected randomly from the first map values, and outputs the difference; wherein the difference is indicative of a neurobehavioural disorder in the subject. The difference may be indicative of the extent to which the subject was guided towards the selected one or more feature while observing the visual scene.

In one embodiment of the above methods and systems, the one or more feature is a saliency feature, the spatial map is a saliency map, and the map values are saliency values. In such embodiment, the difference is indicative of the extent to which the subject was guided towards one or more saliency feature while observing the visual scene.

In the above methods and systems, quantifying a difference may include using an information theoretic measure. The information theoretic measure may be the Kullback-Leibler divergence or ordinal dominance analysis. The difference may be a mathematical measure, such as a ratio.

In the above methods and systems, the visual scene may include a video displayed on a television or computer screen. A spatial map may be generated for each frame of the video, and one or more eye movements recorded for each frame of the video. The video may comprise a series of video clips. Each video clip may be 2 to 4 seconds in length.

In the above methods and systems, the computational model may select one or more feature from the group consisting of a statistical analysis of the gist of the visual scene, detection of human face(s), detection of person(s), detection of animal(s), detection of landscape(s), and detection of text message(s). Quantifying may comprise using a recursive feature elimination-support vector machine.

Also described herein is apparatus for assessing and/or diagnosing a neurobehavioural disorder in a subject, comprising: a visual scene and a spatial map corresponding to the visual scene, the spatial map having first map values that are predictive of eye movement end points of a hypothetical observer observing the visual scene, relative to the one or more feature; an input for receiving data corresponding to eye movements of a subject observing the visual scene; and a processor that quantifies a difference between second map values that correspond to the subject's eye movement endpoints and a set of map values selected randomly from the first map values, and outputs the difference; wherein the difference is indicative of a neurobehavioural disorder in the subject.

In one embodiment of the apparatus, the visual scene may include a video. The apparatus may include means for storing the video, such as a memory device. The apparatus may include hardware for playing a video, such as a CD-ROM or DVD drive. A spatial map may be provided for each frame of the video. The video may comprise a series of video clips. Each video clip may be 2 to 4 seconds in length. The apparatus may include a video display that displays the visual scene. The apparatus may include an eye tracker. The eye tracker may record eye movements of the subject observing the visual scene. The eye tracker may output to the processor data corresponding to eye movements of the subject observing the visual scene. The eye tracker may output data corresponding to eye movements of a subject watching the visual scene to the processor.

The processor may generate the spatial map. In one embodiment, the processor runs a computational model that selects one or more feature in a visual scene and generates the spatial map having first map values that are predictive of eye movement end points of a hypothetical observer relative to the one or more feature.

In the above methods, systems, and apparatus, the neurobehavioural disorder may be Parkinson's disease, Alzheimer's disease, Huntington's disease, fetal alcohol spectrum disorder, attention deficit hyperactivity disorder, schizophrenia, autism, Tourette syndrome, or progressive supranuclear palsy.

BRIEF DESCRIPTION OF THE DRAWINGS

For a better understanding of the invention, and to show more clearly how it may be carried in effect, embodiments will be described below, by way of example, with reference to the accompanying drawings, wherein:

FIGS. 2A-2C show methodology for quantifying agreement between saccades and saliency (or other) maps generated by a computational model through analysis of video images. FIG. 2A: subjects watch video clips and their gaze is recorded. FIG. 2B: each time a saccade starts, the saliency map corresponding to the current video frame being viewed is sampled, around the future endpoint of the saccade. FIG. 2C: chance control samples are also taken at random locations in the saliency map, which allows computation of how significantly above chance the saliency of the saccade target is.

DETAILED DESCRIPTION OF EMBODIMENTS

Overview

Figure 1:
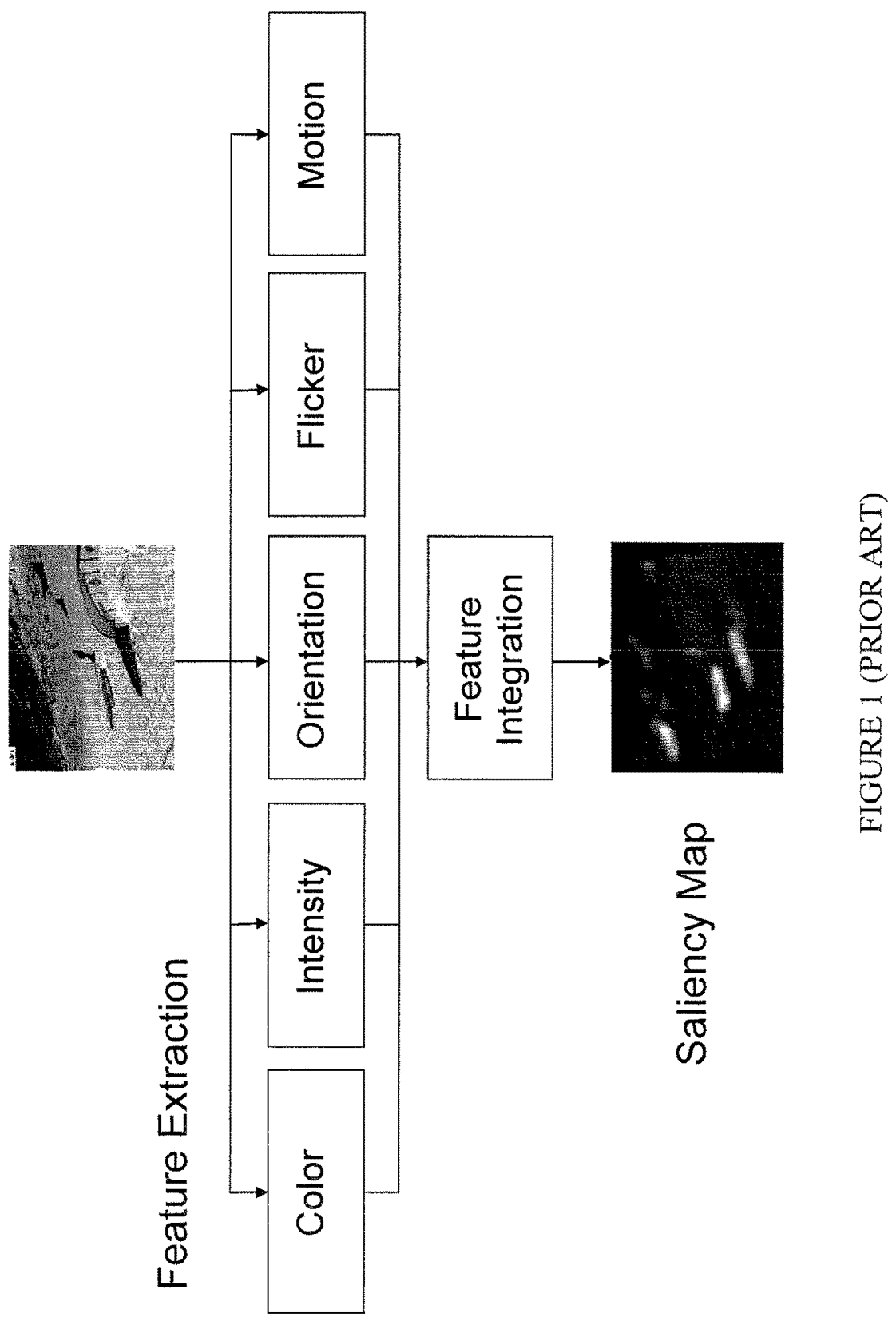
FIG. 1 is a diagrammatic representation of computation of a saliency map from a video frame according to the prior art.

Understanding how the brain develops and ages in normal and diseased humans is a fundamental question in modern neuroscience, with clinical applications to disease prevention, management, and cure. To assess higher brain function it is essential to complement direct probes (e.g., neuroimaging, including functional-MRI) with behavioral evaluations. Behavioral tests typically evaluate subjects through a specific set of cognitive operations. Like neuroimaging, often this is too costly and cumbersome to apply to large populations (for diagnosis or screening), especially when subjects are not living near a large research facility. The invention described herein is based, at least in part, on the premise that brain function and disease state can be quantitatively assessed through much simpler and ecologically-relevant testing.

It is proposed herein that deficits such as response inhibition and shifting attention associated with neurobehavioural disorders such as, for example, PD, FASD, ADHD, schizophrenia, AD, HD, autism, TS, and PSP are based on pathologies of neural substrates that govern how a person would naturally direct attention in an everyday environment. Accordingly, described herein is a task-free method and apparatus for screening and/or diagnosing neurobehavioural disorders such as PD, FASD, ADHD, schizophrenia, AD, HD, autism, TS, and PSP in subjects based on detecting differences in attentional selection mechanisms without having the subjects perform specific tasks, follow instructions, or without an investigator or clinician controlling attention mechanisms. The methods and apparatus described herein facilitate identification of bio-markers of overt visual attention in disorders such as PD, ADHD, FASD, schizophrenia, AD, HD, autism, TS, and PSP.

As described herein, subjects (also referred to herein as "observers" or "participants") freely view visual scenes, while gaze (i.e., patterns of eye movements or "saccades") is monitored. The natural viewing behaviour of each subject is used as a measure of attentional allocation to any object of interest in a given scene, and subsequently to develop classifiers to differentiate patient groups from age-matched controls based on patterns in natural viewing behaviour. This approach eliminates confounds introduced when subjects are required to follow specific, complex instructions or when running contrived experiments in the lab. Further, this approach may be more natural and more sensitive for testing young children and the elderly who cannot perform structured laboratory tasks. Statistical properties of eye movements (e.g., distributions of saccade amplitudes, endpoints, velocities, durations, fixation durations, etc.) are examined, and the extent to which the eyes may be guided towards salient or other types of stimuli (as computed by a saliency model, or other computational model that may evaluate the contents of the visual scene via statistical, image processing, or other computations, including but not limited to, a model that may detect one or more of human faces, people, animals, text messages, or visually attractive items in visual scenes) is investigated.

In one embodiment, the visual scenes are videos viewed on a video display (e.g., a television or computer screen). The videos are composed of short unrelated clips of the same or different duration (e.g., 1-2 seconds, 2-4 seconds, 1-5 seconds, 1-10 seconds, etc.) to reduce "top-down" expectation and emphasize the difference in "bottom-up" gaze allocation at scene change. As used herein, "top-down" refers to neural processes that provide for goal-directed or voluntary behaviour, while "bottom-up" refers to the influence of environmental stimuli (i.e., saliency) that can guide behaviour automatically. Eye gaze is tracked as the subjects freely watch the videos. A computational saliency model is used, which includes computing saliency maps (i.e., topographic maps indicating the locations of highly salient stimuli based on low-level features, such as, for example, color, intensity, orientation, flicker, motion; see Itti and Koch, 2001) for every frame of the video (see FIG. 1), and correlations between saliency and gaze (e.g., saccade endpoint) are computed. Other computational models may be used in replacement of or in conjunction with the saliency model, which may provide different measures of saliency or of other quantities related to the video images. The computational model is run on a computer or microprocessor.

The use of such computational model(s) affords the ability to extract many (e.g., 5, 10, 25, 50, 100, or more) elements or features of attentional allocation from the video frames and to build a classifier that reliably classifies an individual subject. As described herein, a classifier was constructed to classify subjects with a neurobehavioural disorder from control subjects based on gaze. In one embodiment, the classifier used input features such as one or more of (1) saccade statistics, such as saccade amplitude, (2) correlations between saliency maps and gaze, and (3) differences between the gaze distribution of subjects with a disorder and the gaze distribution of age-matched controls.

In one embodiment, subjects' eye movements were recorded while watching 20 minutes of MTV-style videos. Each 30 second continuous video was composed of 2-4 second clip snippets (clippets) of unrelated scenes to minimize prediction and emphasize attention deployment while engaging in a new environement. Saliency maps as described above were computed for every frame, and correlations between saliency and saccade endpoint were computed.

To develop the method, groups of subjects included young adult controls, elderly controls, PD adults, control children, ADHD children, and FASD children. Correlations between saliency and gaze of each subject group were computed and served as features of support vector machine (SVM) classifiers. The leave-one-out method was used to train and test the classifiers. With eye movement traces of less than 15 minutes of videos, results showed that PD subjects could be classified with 97% accuracy relative to age-matched controls. A similar classifier classified ADHD, FASD, and control subjects with 81% accuracy. The results demonstrated the effectiveness of the method using behavioural data gathered in a free-viewing environment to successfully determine the parameters guiding attention in different populations.

The methods described herein may employ a commercially-available eye tracker, such as an ISCAN RK-464™ (ISCAN, Inc., Woburn, Mass.), EyeLink II™ or EyeLink 1000™ (SR Research Ltd., Ottawa, Canada), or Tobii T60, T120, or X120 (Tobii Technology AB, Danderyd, Sweden). The EyeLink 1000 is particularly attractive because subjects do not need to wear any head-mounted apparatus, which is often heavy and bothersome for young subjects, making tracker calibration a challenge with younger children. In addition, an eye-tracking setup can be integrated into a mobile setting for testing in remote communities. This allows testing of subjects even in remote locations (especially the FASD patients). Eye-tracker calibration and raw-data processing (e.g., to extract saccades, eliminate blinks, etc.) may be carried out using known techniques (see, e.g., Chan et al., 2005; Green et al., 2007; Peltsch et al., 2008; Itti, 2005).

Detailed Description

In one embodiment the method employed the previously-described model of bottom-up visual attention, in which a topographic saliency map was computed from the input images (Itti and Koch, 2000; Itti and Koch, 2001; Itti et al., 1998; Koch and Ullman, 1985). This model of saliency has been proven to be extremely powerful in using features (described below) that are close to what the human visual system utilizes to assemble retinal inputs into a perception of a visual scene. In the model, features were combined interactively into a single map of saliency for every frame that correlated with saccadic eye-movements to locations deemed highly salient (Itti and Koch, 2001). For example, the model selected one or more features in a visual scene and generated a spatial map having map values predictive of eye movement end points of a hypothetical observer relative to the one or more features.

Video input was processed in parallel by a number of multiscale low-level feature maps, which detected local spatial discontinuities in various visual feature channels using simulated center-surround neurons (Hubel and Wiesel, 1962; Kuffler, 1953). Twelve neuronal features were implemented, sensitive to colour contrast (red/green and blue/yellow double-opponency, separately), temporal flicker (onset and offset of light intensity, combined), intensity contrast (light-on-dark and dark-on-light, combined), four orientations (0°, 45°, 90°, 135°), and four oriented motion energies (up, down, left, right). (See Itti et al., 1998, Itti and Koch, 2001 for details). These 12 features were combined into five categories: colour (C), flicker (F), intensity (I), orientation (O), and motion (M). Center and surround scales were obtained using dyadic pyramids with nine levels (from level 0, the original image, to level 8, reduced by a factor 256 horizontally and vertically). Center-surround differences were then computed as pointwise differences across pyramid levels, for six combinations of three center and surround scales, yielding six feature maps for each of the visual feature channels. Each feature map was endowed with internal dynamics that operated a strong spatial within-feature and within-scale competition for activity, followed by within-feature, across-scale competition (Itti and Koch, 2000; Itti et al., 1998). As a result, features that initially produced noisy feature maps were reduced to sparse representations of only those locations which strongly stood out from their surroundings. All feature maps were then summed into a unique scalar saliency map. In other embodiments, the saliency model may be replaced or supplemented by other computational models, such as, for example, a model that exploits statistical analyses of the "gist" of the visual scene (i.e., its broad semantic category, such as indoors vs. outdoors, kitchen vs. bedroom, or mountain vs. beach), or that computes alternative measures of saliency, including, but not limited to, detecting items in the visual scene such as human faces, people, animals, landscapes, text messages, visually attractive items, and others. It will be appreciated that these are merely examples of the many types of measures of saliency that may be used.

The analysis asks the following question: each time an observer executes a saccade, how well, relative to chance, could the model predict where that saccade is headed? (see FIG. 2A-2C) An eyetracker was used to record eye movements while subjects freely watched visual scenes, and saliency values were collected at the endpoint (i.e., target) of every saccade. Information theoretic measures (e.g., ordinal dominance analysis; ODA, or the Kullback-Leibler divergence; KL) were used to quantify any differences between a histogram of saliency values collected at the endpoints of saccades, compared to endpoints (i.e., saliency values) collected at random. The ODA measure provided an assessment of the extent to which observers were guided towards salient stimuli while they observed the videos. Notably, this agreement was dependent upon any cognitive task in which the observer may have been engaged, and also revealed differences between populations of observers.

The metric assessment may be refined by not only considering one ODA measure, but also by breaking it down into components: e.g., by feature type (agreement between eye movements and the color feature maps, or the motion feature maps, etc.) and by saliency values (ratio between how often subjects gazed towards low-saliency stimuli compared to what was expected by chance from random control saccades; or for medium-saliency stimuli; or high-saliency ones). For example, 12 (feature maps of 5 categories)×10 (saliency values quantized into 10 bins)=120 measures of agreement between human eye movements and some component of the model can be derived. This can be further broken down into different time slices: for example, the analysis can be restricted to only the first saccade, second saccade, etc. following the onset of a stimulus (or movie clippet); or the first 250 ms, next 250 ms, etc., or to the entire pool of saccades collected over the entire experiment. The data can also be broken down according to stimulus type (e.g., indoor scenes vs. outdoor ones, or scenes which have been independently judged by naïve observers to contain more interesting content towards the center of the display vs. its periphery).

This "model-based" analysis may be complemented by a number of "model-free" analysis factors: e.g., distributions of saccade amplitudes, of fixation durations, main sequence analysis, etc. Together, the collection of model-based and model-free measures constitute an operational "biometric eye-movement signature" of an individual watching a given set of stimuli.

All the measured parameters may be used to train multidimensional classifiers (e.g., support vector machines may be used), to segregate observer populations according to statistical differences in their biometric signatures.

In pilot studies using the model described herein and the associated eye-movement metrics, saliency effects were quantified in the context of complex dynamic scenes by measuring the prediction accuracy of the saliency model of attentional selection.

Pilot classification results. Using a leave-one-out procedure, the classifier was trained to answer two questions: (1) Given eye movement recordings over video clips for a child selected at random, can this child be reliably classified as control, ADHD, or FASD?; and (2) Given eye movement recordings of an elderly subject selected at random, can this subject be reliably classified as control or PD? It was found that a combination of using saliency maps computed with all features, and maps from these features separately, can well differentiate subjects with disorders and control populations. For example, in pilot studies, control vs. ADHD vs. FASD were classified with 81.40% correctness, and control vs. PD were classified with 94% correctness. The study demonstrated that bottom-up visual attention mechanisms are greatly influenced by diseases such as PD, FASD and ADHD.

The invention will be further described by way of the following non-limiting example.

WORKING EXAMPLE

Methods

Experimental Procedures were approved by the Human Research and Ethics Board at Queen's University at Kingston, Ontario, Canada, adhering to the guidelines of the Declaration of Helsinki, and the Canadian Tri-Council Policy Statement on Ethical Conduct for Research Involving Humans.

Sixty approximately 30-second MTV-style video clips were used. These MTV-style clips were composed of clip snippets ("clippet") randomly cut from continuous videos. Thirty 30-second continuous videos (Sony HandyCam DCR-HC211 NTSC, 640×480 pixels, MPEG-1) were recorded with the camcorder set either: immobile on a tripod, to pan at a constant speed (6°/second ranging 120° back and forth horizontally), or to follow particular people on a university campus, a beach, a shopping district, a ski resort, and a desert. These are referred to as filmed videos. Ten other 30-second continuous videos were also recorded from television and video games, referred to as recorded videos. Lengths of clippets from the filmed videos were distributed uniformly from 2-4 seconds, yielding a total of 291 clippets. Each MTV-style clip (approximately 30 seconds) was made by combining 9 to 11 clippets without any temporal gap in between, and there was no more than one clippet included from the same original video. Thirty MTV-style clips were made from the filmed videos only. Another 30 MTV-style clips were made from the 10 recorded videos only in the same way, but contained clippets of different length. The first group of 10 MTV-style clips contained clippets from the 10 recorded videos that had clippet lengths uniformly distributed from 0.5-2.5 seconds (200 clippets). A second group of 10 had clippet lengths from 1-3 seconds to make another 10 MTV-style clips (139 clippets). Finally, a third group of 10 had clippet lengths of 2-4 seconds (93 clippets).

Abrupt transitions (jump cuts) between clippets were deliberately designed to maximize semantic unrelatedness: no attempt was made to conceal the cuts. Using MTV-style clips presents several advantages over longer, continuous shots: it sustains interest of the observers, it de-emphasizes memory-guided saccades while exacerbating stimulus-guided saccades (since memory of the previous clippet is useless to view the next one), and it allows a large number of "first saccades" (purely stimulus-driven ones, at the onset of each new clippet) to be collected while maintaining total viewing time short.

Six groups (3 control groups and 3 patient groups) of participants with normal or corrected-to-normal vision were recruited for the experiment. There were 24 control children (7-14 years), 18 control young adults (20-29 years), 25 elderly control (52-82 years), 20 ADHD children (8-15 years), 14 FASD children (9-15 years), and 15 elderly PD participants (53-80 years). They were compensated financially and were naive to the purpose of the experiment. Three control children, 3 ADHD children, 1 FASD child, and 1 elderly control were discarded because of incomplete tracking of their eye movements for more than half of the MTV-style clips made from filmed videos. Furthermore, four ADHD children with the inattentive subtype (ADHD-I) were removed from further analysis. Another 2 ADHD children and 2 FASD children were also removed from further analysis and classification because they took stimulant medication on the day of experiment. The demographic data of all participants is shown in Table 1.

played the stimuli (corresponding to a 35.14×25.88 cm field of view). Their heads were stabilized on a chin-rest, and they were instructed "watch and enjoy the videos".

Forty MTV-style clips (30 from the filmed clips, 10 from the three groups of recorded clips) were played in random order. Participants were allowed to rest and leave the chin-rest after every 10 clips (about 5 minutes). A nine-point calibration was performed at the beginning of each session. At the beginning of each clip, participants were required to fixate on a grey cross displayed at the center of the screen. However, participants could then look anywhere on the screen at the beginning of a clippet.

Instantaneous gaze position was tracked by a head-mounted EyeLink II (SR Research Ltd., Ottawa, ON, Canada) (250 Hz, noise<0.022°, gaze position accuracy<0.5° average, and gaze tracking ranges±20° horizontal and ±18° vertical) from the participants' right eye. Data were discarded if gaze position accuracy was off by >1° for any point in the calibration routine. Four thousand eye movement traces (100 participants×40 clips) were obtained. Eye-movement traces from the recorded clips (1,000 eye traces, 100 participants×10 clips) were discarded because of different clippet lengths. Eye movement traces containing excessive (>10%) loss of tracking were removed (197 eye traces), and participants were removed as described above. The remaining 2809 eye movement traces (from 15-30 clips for each participant) were further analyzed and classified as fixation, saccade, blink/artifact, saccade during blink, smooth pursuit, and eye tracker drift/misclassification. Blinks were identified as whenever the pupil diameter was zero, and removed from analysis. Gaze position outside of 1° inside of the border of the screen was labeled as an artifact and removed. Eye movements whose minimum velocity was 30°/s and minimum amplitude was 2° were labelled as saccades. In the end, 162,753 saccades were obtained.

TABLE 1

Demographic data of participants

| Category | Control Elderly | PD | Control Young | Control Children | ADHD | FASD |
|---|---|---|---|---|---|---|
| n | 24 | 15 | 18 | 21 | 12 | 10 |
| age ± SD (year) | 70.33 ± 7.53 | 68.00 ± 6.75 | 23.17 ± 2.52 | 10.19 ± 2.06 | 11.08 ± 1.80 | 12.60 ± 1.56 |
| male:female | 11:13 | 10:5 | 8:10 | 7:10 | 11:1 | 3:7 |
| subtype | | | | | inattentive*: 0 | **FAS: 5 |
| | | | | | hyperactive: 0 | pFAS: 1 |
| | | | | | combined: 12 | ARND: 4 |
| medication† | | None: 0 | | | None: 4 | None: 9 |
| | | Amandadine: 1 | | | NE-RI: 1 | Stimulant: 1 |
| | | Clonazepam: 1 | | | Stimulant-CR: 6 | |
| | | Entacapone: 1 | | | Amphetamine-DX: 1 | |
| | | Ldopa/carbidopa: 10 | | | | |
| | | Ldopa/carbidopa-CR: 2 | | | | |
| | | Pramipexole: 2 | | | | |
| | | Ropinirole HCl: 9 | | | | |
| co-morbidity score | | UPDRS motor: 25.36 ± 6.61 | | | ODD: 3 | ADHD: 4 |
| | | Hoehn and Yahr stage: 2.36 ± 0.36 | | | | |

*Inattentive-type ADHD patients were removed from analysis.
**Fetal Alcohol Spectrum Disorder can be subdivided, clinically, into Fetal Alcohol Syndrome (FAS), partial Fetal Alcohol Syndrome (pFAS), and Alcohol Related Neurodegeneration (ARND).
† For the 3 children populations, "None" indicates the child had never taken medication for the disorder. If medication was taken regularly, but not on the day of the experiment, they were included. If medication was taken on the day of the experiment, they were removed from the experiment. For the two elderly populations (PD and elderly controls), subjects were included even if they took medication on the day of the experiment.

Data Acquisition. Participants sat approximately 60 cm in front of an 18-inch color monitor (363×271 mm) that dis- Computing Saliency Maps from Stimuli. The Itti and Koch (2001) saliency model was used to compute saliency maps of each low-level feature or combination of features for every video frame, using the iLab C++ Neuromorphic Vision Toolkit (available from University of Southern California; see http://ilab.usc.edu/toolkit/home.shtml). Saliency maps computed from individual low-level features included color (C), intensity (I), orientation (O), flicker (F), motion (M), variance, spatial correlation (16×16 pixel-wise correlations of similar intensity values), and four types of junctions (L, T, X, E). Moreover, saliency maps were also computed from combined features CIOFM, and a Surprise version of CIOFM, which not only takes spatial distribution of features into account, but also the temporal change of the features.

Figure 3B:
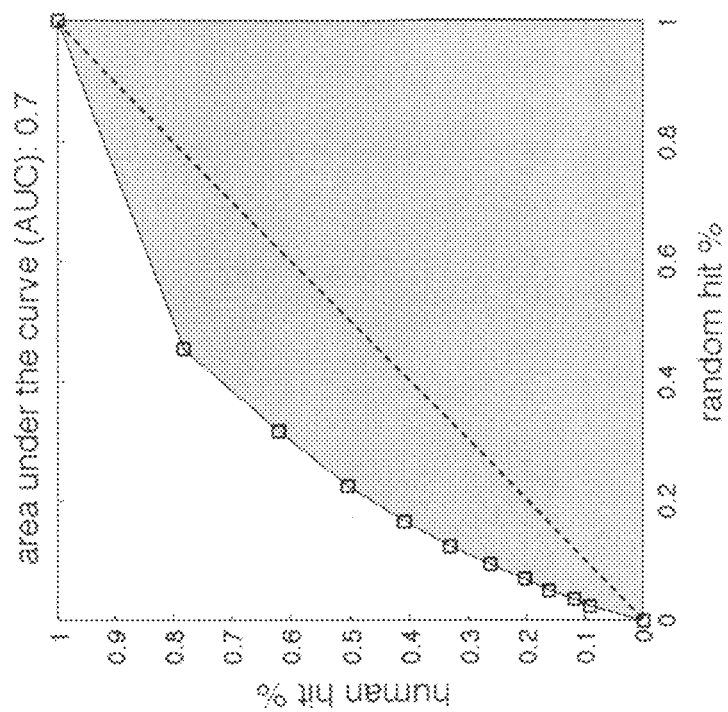
FIG. 3B is a plot showing an ordinal dominance curve generated by sliding an incremental threshold from 0 to 1 on the histograms of FIG. 3A, and computing the percentage of map values above each threshold. A map value larger than threshold is a "hit". The vertical axis is the percentage of participant hits, and the horizontal axis is the percentage of random hits. The area under the curve (AUC) shows the predictability of the maps in subjects' saccade endpoints, and it was defined as the correlation between saliency and gaze.
Figure 3A:
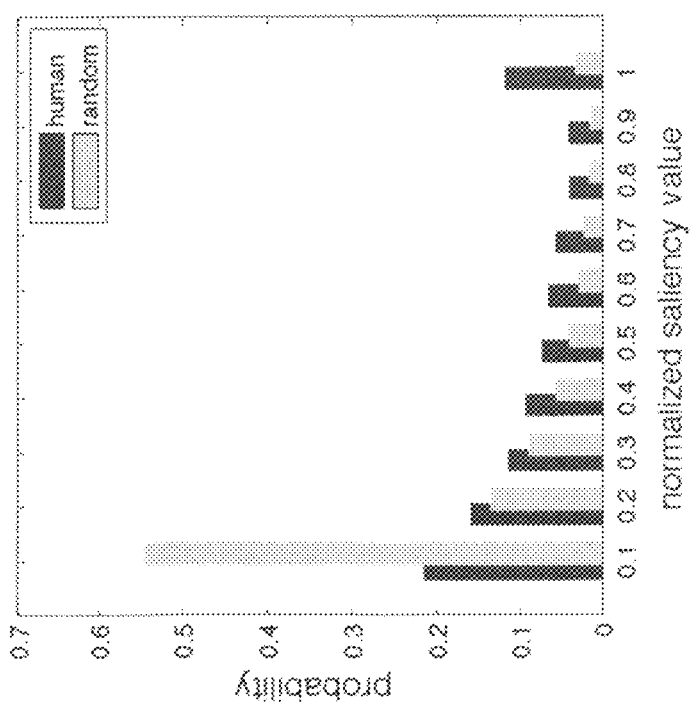
FIG. 3A is a histogram showing probability of normalized saliency map values corresponding to saccade endpoints for a subject, compared to normalized random saliency values.

Computing Model-Based Features. Correlation between saliency and gaze was computed using ordinal dominance analysis (Bamber, 1975). When a participant initiated a saccade, a map value at saccade endpoint (max value in a 2.5° circular window) was obtained and compared to 100 map values that were randomly and uniformly sampled from the map. These map values were normalized from 0 to 1 by the minimum and maximum values of the map. With all the saccades, a subject ("human") histogram and a random histogram were generated from normalized map values (FIG. 3A). To create an ordinal dominance curve, an incremental threshold was slid from 0 to 1 on both histograms and the percentage of the map values above each threshold was computed. A map value larger than threshold was called a "hit". The vertical axis of the rotated ordinal dominance curve was the percentage of participant hits, and the horizontal axis was the percentage of random hits (see FIG. 3B). The area under the curve (AUC) shows the predictability of the maps in participants' saccade endpoints, and it was defined as the correlation between saliency and gaze. An AUC of 0.5 meant the maps predicted saccade endpoint no better than random. An AUC above 0.5 meant the maps predicted saccade endpoints better than random (and vice versa).

In addition to the AUC that summarized the difference between histograms, the difference in each bin of the histogram was also computed. A coarse version of the histograms that had only 3 bins was generated, and the observer histogram was subtracted by random histogram. The differences in the two bins with higher map values were later used as classifier features. The difference in the histogram gave the classifier more information about the shape of curve in addition to the summary of the AUC.

Computing Model-Free Features. Two types of model-independent features were utilized for classification: saccade statistics, and difference in gaze distribution (diffGaze) from the young adult controls. For saccade statistics, the median and inter-quartile difference in peak velocity, saccade amplitude, saccade duration and saccade interval were used. The saccade interval for the 1st saccade is the duration from the onset of a new scene (new clippet) to the initiation of the first saccade. The inter-observer difference was quantified by an AUC with a map generated by instantaneous eye positions of the young adult controls.

Clippet Selection for Comparing FASD and ADHD. For the classification of PD patients and elderly controls (and the initial classification of FASD versus ADHD), all clippets were used. However, to improve the classification of FASD from ADHD, the analysis was also conducted using only a subset of clippets. Scenes in a given clippet could be simple or complex in terms of number of objects of interest that attract a participant's attention. If there was only one object of interest in a scene (where all saccades were directed to) the clippet was considered too simple to be useful in differentiating populations based on gaze. However, as it is difficult to come up with a proper determination of the number of objects of interest a priori, the gaze distribution of the young adult control group was also utilized for selecting clippets that might contain multiple objects of interest. Low inter-observer differences in gaze distribution implied low numbers of objects of interest. Hence, the top 25% of clippets from filmed clips that had the highest inter-participant difference in controlling young adults' gaze distribution were selected.

Classification and Feature Selection.

SVM, leave-one-out: linear kernel support vector machines (SVM) (Cortes, 1995; Vapnik, 1995, 1998) were used to perform classification analysis. For classifying ADHD, FASD, and control children, two classifiers were built. The first classifier determined whether a participant had a disorder (FASD, ADHD) or was a control. If the participant had a disorder, the second classifier determined whether the disorder was ADHD or FASD. Given the small number of participants in each group, the leave-one-out method was used to train and test the performance of the classifiers.

feature for classifiers: As outlined above, the model-dependent features for the classifiers were the median AUC of the 3rd to 5th saccade with saliency maps of C, I, O, F, M, L, T, X, E, variance, spatial correlation, CIOFM and the 'Surprise' version of CIOFM (3 saccades×13 features). For the second analysis conducted on FASD and ADHD, the difference in a participant histogram and a random histogram for each feature was also included (3 saccades×13 features×3 bins). The model-independent features included the median and inter-quartile differences in peak velocity, saccade amplitude, saccade duration, and saccade interval of the first saccade (1 saccade×8 features). In addition, the AUC of the inter-observer difference from the 3rd to 5th saccades (3 saccades×1 features) was included. Data after the 6th saccade were discarded because of the small number of saccades, and data for the first two saccades were also discarded because of a strong center bias after the onset of a new scene. However, for saccade statistics, only the first saccade was considered so that the reaction time of a saccade initiated from the onset of a new scene could be calculated. Feature values were first normalized to a z-score such that the mean and standard deviation were computed, and then passed by an arctangent function to diminish the effect of outliers. Outliers were defined as values smaller than the lower quartile minus 1.5 times inter quartile difference, or larger than upper quartile plus 1.5 times inter quartile difference.

feature selection: Feature selection was performed to find features the most useful in differentiating populations. A commonly used feature selection algorithm support vector machine—recursive feature elimination (SVM-RFE; Guyon, 2002) was utilized. After training a SVM classifier, the feature with smallest weight in absolute value was discarded because it was least important in computing a decision boundary. In the next iteration, the SVM classifier was trained again and the feature with the smallest weight was discarded. The procedure continued until the features were depleted, and the last ones to be discarded were identified as the most important features in differentiating populations.

feature used for Parkinson's study: For classifying PD from elderly control participants, 39 (3rd-5th saccades, 13 features) model-dependent features were included, as were 8 (1st saccade, 8 features) features of saccade statistics, and 3 (3rd-5th saccades, 1 feature) features of inter-observer gaze differences. Fifty features were used in the end. Features were computed from all the filmed clippets. Features were also normalized as per the method described above.

feature used for ADHD FASD: For the hierarchical classifiers classifying ADHD, FASD, and control children, two classifiers performed SVM-RFE independently from each other. To improve classification accuracy, specific clippets were selected as described above, and features were also computed from the difference in histogram. Saccade statistics computed from all but the 1st saccade were also included. In the end, 184 features were used in the classifier.

Results

Classification of PD and Control Elderly. The values of the three types of input features were normalized to z-scores, and the influence of outliers was reduced by applying an arctangent function. Features of saccade statistics included the medium and inter-quartile difference of saccade amplitude, peak velocity, saccade duration, and time to saccade initiation from a scene change. Only the first saccade after the scene change was used to compute these statistics (see Methods). For computing the correlation between saliency and gaze, saliency maps were computed from the low-level features: color (C), intensity (I), orientation (O), flicker (F), motion (M), variance, spatial correlation (Scorr), and 4 types of line junctions (L, T, X, E). Additionally, saliency maps were also computed from the combined features CIOFM, and from a 'Surprise' version of CIOFM (Itti, 2005; Itti and Baldi, 2009), which takes the temporal change of the features into account. Next, the correlation between gaze and these saliency maps was computed. To compute features of difference between gaze (diffGaze), a map of gaze distribution from healthy young adults was generated at each time point, and the difference was computed as the correlation between gaze (of PD or control elderly) and the map (see Methods). For features of the correlation and difference in gaze, only those computed from the 3rd, 4th, and 5th saccades following a scene change were used by the classifier, due to the fact that the first two saccades upon a scene change contained elements of center bias (Tseng et al., 2009). Saccades after the 6th were discarded because they were too few in number.

Figure 4:
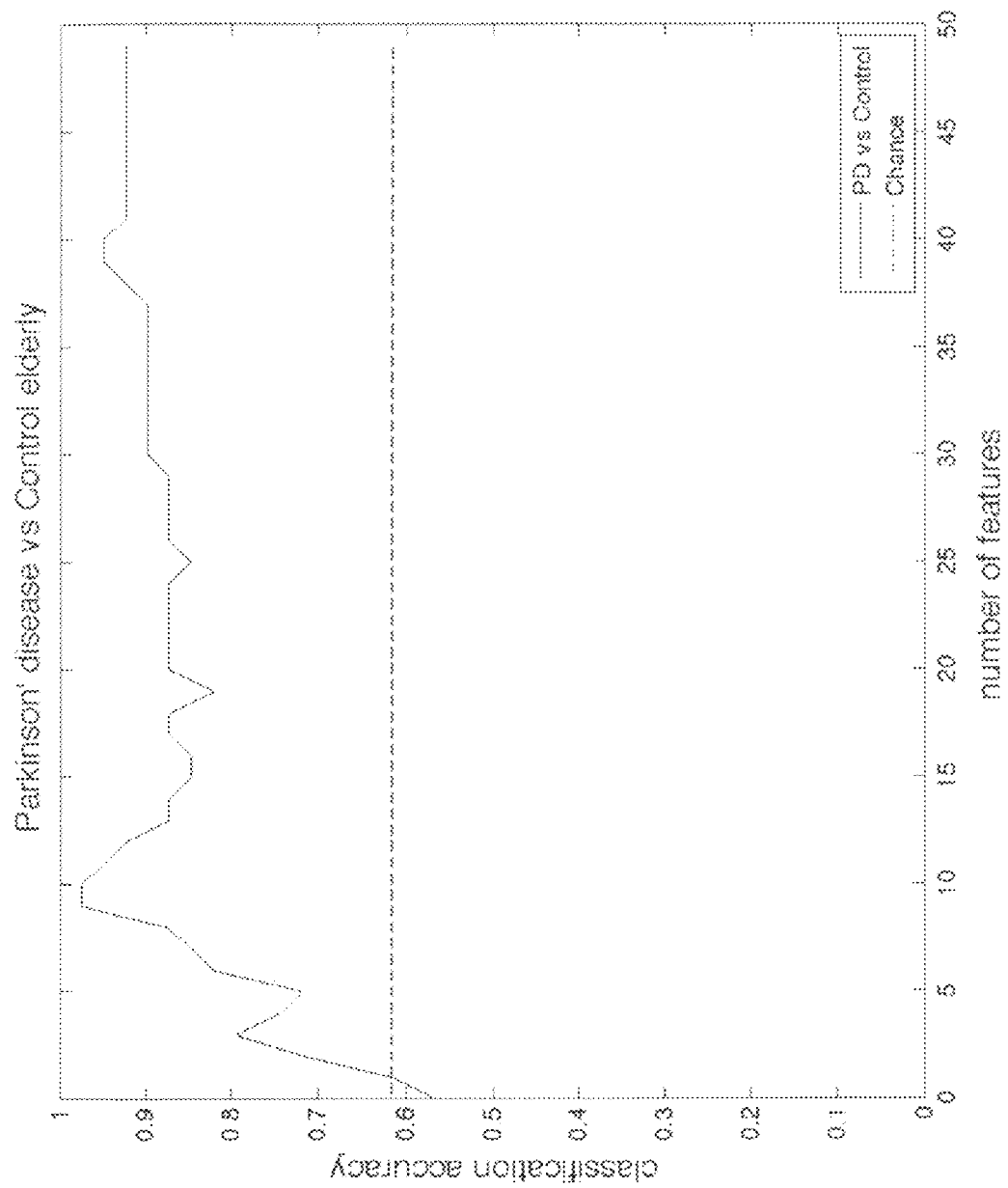
FIG. 4 is a plot showing classification accuracy of PD and age matched elderly controls with a feature selection process (recursive feature elimination-support vector machine). The plot shows classification accuracy with all features included (right most) and as features are eliminated (moving leftwards).

The distribution of normalized feature values for PD and age matched controls showed that both the PD and elderly control groups had participants with very high z-scores, and very low z-scores. Nevertheless, PD subjects had a smaller proportion of participants with high z-scores for saccade statistics and correlation between saliency, but a greater proportion with high z-scores for the difference in gaze distribution compared to that of young adults. The SVM classifier was able to reach 97.44% classification accuracy with 15 minutes of eye movement data (FIG. 4). With the initial feature sets, the classifier performed better than 90% classification accuracy as tested by leave-one-out cross validation. To identify the most useful features in differentiating PD and control elderly, a feature selection method, recursive feature elimination-support vector machine (RFE-SVM), was used. RFE-SVM first trained a classifier with all the features and obtained weights of each feature. Then, a feature with the smallest absolute weight was discarded. In the next iteration, the classifier was trained again with the remaining features, and a feature with smallest absolute weight in the remaining set was discarded. The elimination process continued until features were depleted. The classification accuracy reached a peak when the top 10 or top 11 features were used. Results of this process are shown graphically in FIG. 6.

Selected Features in Differentiating PD and Control Elderly. The top 10 features selected by RFE-SVM are shown in Table 2 and the statistics are listed below. In addition, for difference between gaze, the feature diffGaze was also selected. For features of saccade statistics, the two features of saccade duration were both selected. For features of correlation between saliency and gaze, all three features of orientation were selected, and spatial correlation, color, and motion were also selected.

TABLE 2

Top features from feature selection for classifying PD and control elderly.

| Rank (std) | Feature | Saccade Index |
| --- | --- | --- |
| 1.6667 (1.4018) | orientation | 3 |
| 2.0256 (0.5374) | spatial correlation | 4 |
| 3.3846 (0.90657) | spatial correlation | 5 |
| 4.3846 (1.7262) | diffGaze | 4 |
| 5.4872 (1.8191) | saccade duration | 1 |
| 8.641 (3.2726) | motion | 3 |
| 8.6923 (3.6646) | orientation | 4 |
| 9.7949 (2.1665) | orientation | 5 |
| 11.3333 (3.8888) | color | 3 |
| 11.641 (5.494) | color | 4 |
| 12.9231 (4.7594) | saccade duration inter-quartile difference | 1 |

Classification Results for PD and Control Elderly.
Best classification accuracy (PD vs control elderly): 97.4359% (chance: 61.5385%)

Classification of ADHD, FASD and Control Children. The above analyses were repeated using the same features to classify ADHD and FASD children, and the classifier achieved an accuracy of 59.09% percent (i.e., slightly better than chance, 54.54%). However, using additional input features and only a subset of clippets (those that with young adult controls contained 25% diverse gaze distribution) improved classification accuracy to 84%. The subset of clippets included eye movement traces from 3.75 minutes of videos.

Because diverse gaze distribution among individuals might represent multiple objects of interest in a scene, the multiple objects of interest compete for attentional allocation. This means that these complex scene clippets likely reveal more difference in attentional allocation among different populations. To do a 3-class classification with binary SVM classifier, a hierarchical classifier with two binary SVMs was constructed. The first SVM classified whether the subject was a control or had a disorder; if the subject had a disorder, then the 2nd classifier determined whether the subject was a ADHD or FASD child. The classifiers took model-dependent and also, model-independent features as input. Model-dependent features included correlation between various saliency and gaze computed by the saliency model. Model-independent features included basic saccade statistics and the difference in gaze distribution between the children (patient or control) and a group of young adults (see Methods for details).

Figure 5:
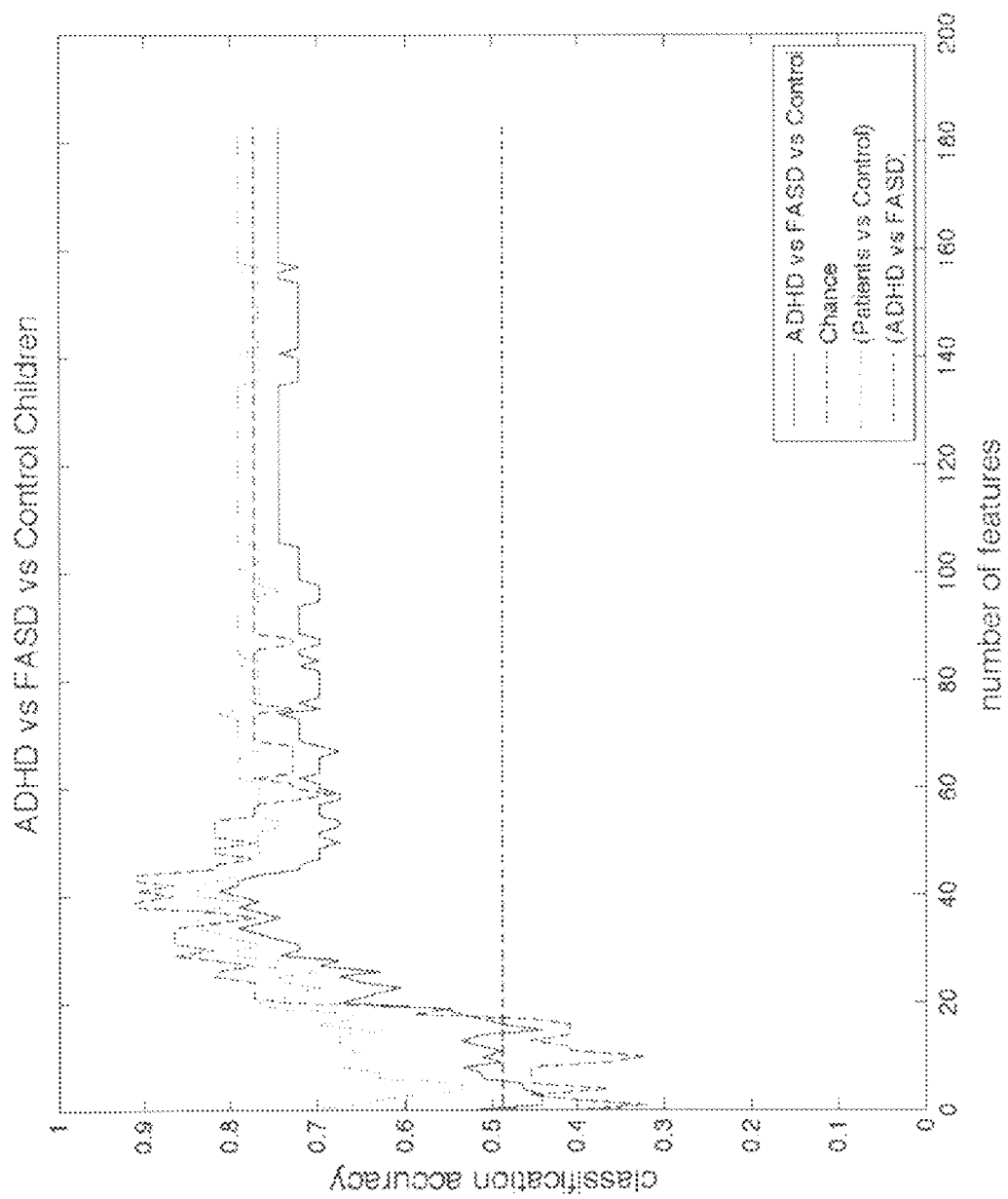
FIG. 5 is a plot showing classification accuracy of control, ADHD, and FASD children with a feature selection process (recursive feature elimination-support vector machine). The plot shows classification accuracy with all features included (right most) and as features are eliminated (moving leftwards).

To find the most useful features in different populations and to boost classification accuracy, support vector machine-recursive feature elimination (SVM-RFE) was used to select a subset of best features. The two classifiers eliminate features independently, and the result is shown in FIG. 5. In the process of eliminating features, the classification accuracy reached 84% (chance: 47.73%) in 3-class classification (ADHD, FASD, and control children). The statistics are listed below.

TABLE 3

Top features from feature selection for classifying ADHD, FASD, and control children. Hist# represents the #th bin of a histogram.

| Classifier 1: patients vs control (Best Classification Accuracy: 83.72%) | | | Classifier 2: ADHD vs FASD (Best Classification Accuracy: 90.91%) | | |
|---|---|---|---|---|---|
| Rank (std) | Feature | Saccade Index | Rank (std) | Feature | Saccade Index |
| 5.4186 (3.7748) | F hist3 | 4 | 10.3636 (8.0802) | O hist3 | 4 |
| 5.6512 (5.9956) | F hist3 | 3 | 10.4091 (7.9021) | sacint | 2 to end |
| 9.2791 (4.7476) | EyeMvt hist1 | 5 | 10.5 (10.0036) | E hist1 | 4 |
| 9.5814 (7.1821) | Scorr hist3 | 3 | 10.9091 (8.7009) | X hist1 | 5 |
| 10.7442 (7.1083) | surprise hist2 | 4 | 11.8182 (7.8233) | Scorr hist2 | 5 |
| 10.8605 (6.9645) | F hist2 | 3 | 12.3182 (8.61) | CIOFM hist2 | 4 |
| 11 (9.0738) | surprise hist3 | 3 | 14.1364 (9.7653) | F hist3 | 4 |
| 11.5349 (6.8221) | F hist2 | 4 | 14.1818 (8.661) | Variance hist3 | 4 |
| 13.0233 (8.7709) | Variance hist2 | 3 | 15 (13.8495) | M hist2 | 5 |
| 13.2558 (10.4792) | Scorr | 3 | 15.0909 (13.3378) | F | 5 |

CONCLUSION

The results demonstrate a robust classification of subjects by age and disease groups: child vs. young adult vs. elderly; controls vs. PD; controls vs. ADHD vs. FASD). This is significant because ADHD and FASD are often co-morbid with other behavioral problems, as well as with each other (see Table 1). Thus, prior to the embodiments described herein, differential diagnosis has been difficult.

The results demonstrate that attentional selection mechanisms are influenced by PD, ADHD, and FASD, and the behavioral differences can be captured by the correlation between saliency and gaze. Furthermore, the results confirm that a task-free method can be used as a screening tool for clinical disorders in both children and elderly populations.

All cited publications are incorporated herein by reference in their entirety.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

REFERENCES

Bamber, D. (1975) The area above the ordinal dominance graph and the area below the receiver operating characteristic graph. *Journal of Mathematical Psychology* 12:387-415.

Chan, F., Armstrong, I. T., Pari, G., Riopelle, R. J., and Munoz, D. P. (2005) Saccadic eye movement tasks reveal deficits in automatic response inhibition in Parkinson's disease. *Neuropsychologia* 43:784-79'6.

Cortes, C., Vapnik, V. (1995) Support-vector networks. *Machine Learning* 20:273-297.

Green, C. R., Munoz, D. P., Nikkel, S. M., and Reynolds, J. N. (2007) Deficits in eye movement control in children with Fetal Alcohol Spectrum Disorders. *Alcoholism: Clinical and Exp. Res.* 31:500-511.

Guyon, I., Weston, J., Barnhill, S., Vapnik, V. (2002) Gene selection for cancer classification using support vector machines. *Machine learning* 46:389-422.

Hubel, D. H., Wiesel, T. N. (1962) Receptive fields, binocular interaction and functional architecture in the cat's visual cortex. *J. Physiol.*, 160:106-154.

Itti, L. (2005) Quantifying the Contribution of Low-Level Saliency to Human Eye Movements in DynamicScenes. *Visual Cognition*, 12(6):1093-1123.

Itti, L., Koch, C., Niebur, E., et al. (1998) A model of saliency-based visual attention for rapid scene analysis. *IEEE Transactions on pattern analysis and machine intelligence* 20:1254-1259.

Itti, L., Koch, C. (2000) A saliency-based search mechanism for overt and covert shifts of visual attention. *Vision Research*, 40(10-12):1489-1506.

Itti, .L, Koch, C. (2001) Computational modelling of visual attention. *Nat Rev Neurosci* 2:194-203.

Itti, L., Baldi, P. (2005) *A principled approach to detecting surprising events in video* (Citeseer), 1:631.

Itti, L., Baldi, P. (2009) Bayesian surprise attracts human attention. *Vision Res* 49:1295-306.

Koch, C., Ullman, S. (1985) Shifts in selective visual attention: towards the underlying neural circuitry. *Hum Neurobiol*, 4(4):219-27.

Kuffler, S. W. (1953) Discharge patterns and functional organization of the mammalian retina, *J. Physiol.* 16:37-68.

Peltsch, A., Hoffman, A., Armstrong, I., Pari, G., and Munoz, D. P. (2008) Saccadic impairments in Huntington's disease correlate with disease severity. *Exp. Brain Res.* 186:457-469.

Tseng, P. H., Carmi, R., Cameron, I. G. M., Munoz, D. P., Itti, L. (2009) Quantifying center bias of observers in free viewing of dynamic natural scenes. *J Vis* 9:4.

Vapnik, V. (1995) *The Nature of Statistical Learning Theory* (Springer-Verlag, New York).

Vapnik, V. (1998) *Statistical Learning Theory* (Wiley-Interscience).

The invention claimed is:

1. A method of assessing, diagnosing, or assessing and diagnosing a neurobehavioural disorder in a subject, comprising:
   using a processor-based computational model to select one or more feature in a visual scene and generate a spatial map having first map values that are predictive of eye movement end points of a hypothetical observer relative to the one or more feature;
   recording the subject's eye movements while the subject freely observes the visual scene; and
   generating second map values that correspond to the subject's eye movement endpoints that do not rely on the subject performing a task;
   quantifying a difference between the second map values and a set of map values selected randomly from the first map values;
   wherein the difference is indicative of a neurobehavioural disorder in the subject.

2. The method of claim 1, wherein the difference is indicative of the extent to which the subject was guided towards the selected one or more feature while observing the visual scene.

3. The method of claim 1, wherein the one or more feature is a saliency feature, the spatial map is a saliency map, and the map values are saliency values.

4. The method of claim 3, wherein the difference is indicative of the extent to which the subject was guided towards one or more saliency feature while observing the visual scene.

5. The method of claim 1, wherein the visual scene includes a video displayed on a television or computer screen.

6. The method of claim 5, wherein a spatial map is generated for each frame of the video, and one or more eye movements are recorded for each frame of the video.

7. The method of claim 6, wherein the video comprises a series of video clips.

8. The method of claim 1, wherein the computational model selects one or more feature from the group consisting of a statistical analysis of the gist of the visual scene, detection of human face(s), detection of person(s), detection of animal(s), detection of landscape(s), and detection of text message(s).

9. The method of claim 1, wherein the neurobehavioural disorder is selected from Parkinson's disease, Alzheimer's disease, Huntington's disease, fetal alcohol spectrum disorder, attention deficit hyperactivity disorder, schizophrenia, autism, Tourette syndrome, and progressive supranuclear palsy.

10. Apparatus for assessing, diagnosing, or assessing and diagnosing a neurobehavioural disorder in a subject, comprising:
    a visual scene and a spatial map corresponding to the visual scene, the spatial map having first map values that are predictive of eye movement end points of a hypothetical observer observing the visual scene, relative to the one or more feature;
    an input for receiving data corresponding to eye movements of a subject observing the visual scene, the data including second map values that correspond to the subject's eye movement endpoints that do not rely on the subject performing a task; and
    a processor that quantifies a difference between the second map values and a set of map values selected randomly from the first map values, and outputs the difference;
    wherein the difference is indicative of a neurobehavioural disorder in the subject.

11. The apparatus of claim 10, wherein the visual scene includes a video.

12. The apparatus of claim 11, wherein a spatial map is provided for each frame of the video.

13. The apparatus of claim 11, wherein the video comprises a series of video clips.

14. The apparatus of claim 10, including a video display that displays the visual scene.

15. The apparatus of claim 10, including an eye tracker that records eye movements of the subject observing the visual scene, or outputs to the processor data corresponding to eye movements of the subject observing the visual scene.

16. The apparatus of claim 10, wherein the neurobehavioural disorder is selected from Parkinson's disease, Alzheimer's disease, Huntington's disease, fetal alcohol spectrum disorder, attention deficit hyperactivity disorder, schizophrenia, autism, Tourette syndrome, and progressive supranuclear palsy.

17. The apparatus of claim 10, further comprising a computer program stored on non-transitory storage media compatible with the processor, the computer program containing instructions to direct the processor to use a computational model to select one or more feature in the visual scene and generate the spatial map having first map values that are predictive of eye movement end points of a hypothetical observer relative to the one or more feature.

18. A method of assessing, diagnosing, or assessing and diagnosing a neurobehavioural disorder in a subject, comprising:
    monitoring the subject's eye movements while the subject freely observes a visual scene and preparing second map values that correspond to the subject's eye movement endpoints, wherein the second map values correspond to the subject's eye movement endpoints that do not rely on the subject performing a task;
    quantifying a difference between the second map values and a set of first map values;
    wherein the first map values were obtained using a processor-based computational model that selects one or more feature in the visual scene and generates spatial map values comprising the first map values, the spatial map values being predictive of eye movement end points of a hypothetical observer relative to the one or more feature;
    wherein the difference is indicative of a neurobehavioural disorder in the subject.

19. The method of claim 18, wherein the set of first map values are randomly selected from the spatial map values.

20. The method of claim 18, wherein the difference is indicative of the extent to which the subject was guided towards the selected one or more feature while observing the visual scene.

21. The method of claim 18, wherein the one or more feature is a saliency feature, the spatial map is a saliency map, and the map values are saliency values.

22. The method of claim 21, wherein the difference is indicative of the extent to which the subject was guided towards one or more saliency feature while observing the visual scene.

23. The method of claim 18, wherein the visual scene includes a video displayed on a television or computer screen, or a series of video clips displayed on a television or computer screen.

24. The method of claim 23, wherein a spatial map is generated for each frame of the video, and one or more eye movements are recorded for each frame of the video.

25. The method of claim 18, wherein the neurobehavioural disorder is selected from Parkinson's disease, Alzheimer's disease, Huntington's disease, fetal alcohol spectrum disorder, attention deficit hyperactivity disorder, schizophrenia, autism, Tourette syndrome, and progressive supranuclear palsy.

* * * * *